United States Patent [19]
Gjerde

[11] Patent Number: 5,338,448
[45] Date of Patent: Aug. 16, 1994

[54] METHOD OF PREVENTING CONTAMINATION OF A CHROMATOGRAPHY COLUMN
[75] Inventor: Douglas T. Gjerde, Saratoga, Calif.
[73] Assignee: Sarasep, Inc., Santa Clara, Calif.
[21] Appl. No.: 52,601
[22] Filed: Apr. 27, 1993

Related U.S. Application Data
[63] Continuation-in-part of Ser. No. 962,097, Oct. 16, 1992, abandoned.
[51] Int. Cl.[5] .............................................. B01D 15/08
[52] U.S. Cl. .................................. 210/198.2; 210/656; 96/101; 96/102
[58] Field of Search ................... 210/656, 198.2, 502.1; 96/101, 102; 422/70

[56] References Cited

U.S. PATENT DOCUMENTS

| | | | |
|---|---|---|---|
| 3,440,864 | 4/1969 | Blume | 210/198.2 |
| 3,470,864 | 10/1969 | Emmert | 126/110 |
| 3,487,938 | 1/1970 | Patterson | 210/198.2 |
| 3,511,377 | 5/1970 | Hrdina | 210/198.2 |
| 4,116,837 | 9/1978 | Biermacher | 210/198.2 |
| 4,354,932 | 10/1982 | McNeil | 210/198.2 |
| 4,384,957 | 5/1983 | Crowder | 210/198.2 |
| 4,448,691 | 5/1984 | Davis | 210/198.2 |
| 4,451,365 | 5/1984 | Sattler | 210/198.2 |
| 4,457,846 | 7/1984 | Munk | 210/198.2 |
| 4,554,071 | 11/1985 | Ruijten | 210/198.2 |
| 4,565,632 | 1/1986 | Hatch | 210/198.2 |
| 4,636,316 | 1/1987 | Harris | 210/198.2 |
| 4,639,513 | 1/1987 | Hou | 530/387 |
| 4,663,163 | 5/1987 | Hou | 210/198.2 |
| 4,710,289 | 12/1987 | Wermuth | 210/198.2 |
| 4,737,284 | 4/1988 | Hauke | 210/198.2 |
| 4,743,373 | 5/1988 | Rai | 210/198.2 |
| 4,758,340 | 7/1988 | Marchand | 210/198.2 |
| 4,789,479 | 12/1988 | Onitsuka | 210/198.2 |
| 4,806,238 | 2/1989 | Sattler | 210/198.2 |
| 4,894,152 | 1/1990 | Colvin | 210/198.2 |
| 4,957,620 | 9/1990 | Cussler | 210/198.2 |
| 5,053,133 | 10/1991 | Klein | 210/198.2 |
| 5,059,654 | 10/1991 | Hou | 210/198.2 |
| 5,071,547 | 12/1991 | Cazer | 210/198.2 |
| 5,071,610 | 12/1991 | Hagen | 210/198.2 |
| 5,171,440 | 12/1992 | Kawamura | 210/198.2 |
| 5,238,621 | 8/1993 | Hagen | 210/198.2 |
| 5,242,586 | 9/1993 | Ransohoff | 210/198.2 |

OTHER PUBLICATIONS

"MemSep Chromatography Cartridges" Milipore Advertisement (1990), Lit. No. PB084 Rev. 5/90 90-286, pp. 1-8.
*Forum*, (1992), 12, "When Should Guard Columns be Replaced", Mac Mod Analytical, Inc., pp. 1-4.
*Journal of Chromatography*, (1991), 555, pp. 97-107, "High-Performance Membrane Chromatography of Proteins, A Novel Method of Protein Separation" Tennikova et al.
*Analytica Chimica Acta*, (1990), 236, pp. 157-164, "Membrane Approach to Solid-Phase Extractions", Hagen et al.
*Journal of Liquid Chromatography*, (1990), 13, pp. 63-70, "High-Performance Membrane Chromatography, A Novel Method of Protein Separation", Tennikova et al.
*Biomedical Products*, (1992), pp. 42, "The Use of Microporous Plastic PVC-Silica Sheets for Ion Exchange and Affinity Chromatography of Proteins and Antibodies", Goldberg et al.
*Journal of Chromatographic Science*, (1991), 29:444-449, "Application of a Novel Form of Solid-Phase Sorbent (Empore Membrane) to the Isolation of Tricyclic Antidepressant Drugs from Blood", Lensheyer et al.
*American Laboratory*, "High Performance Membrane Chromatography", pp. 30-31, Joachim Reusch, undated.
*Therapeutic Drug Monitoring*, (1991), 13:244-250, "Application of the Empore Solid-Phase Extraction Membrane to the Isolation of Drugs from Blood, I. Amiodarone and Desethylamiodarone" Lensmeyer et al.

*Primary Examiner*—Ernest G. Therkorn
*Attorney, Agent, or Firm*—Oblon, Spivak, McClelland, Maier & Neustadt

[57] ABSTRACT

Liquid chromatography separation columns can be protected from contamination with particulate and dissolved contaminants by the use of a thin protective pad which removes contaminants from a sample stream prior to separation of the sample on the separation column. The protective pad may be in the form of a guard disk positioned inline or directly contacting the separation column.

22 Claims, 5 Drawing Sheets

NO GUARD

8 MINUTES

WITH GUARD DISK

8 MINUTES

WITH GUARD COLUMN

8 MINUTES

NO GUARD

4 MINUTES

WITH GUARD DISK

4 MINUTES

METHOD OF PREVENTING CONTAMINATION OF A CHROMATOGRAPHY COLUMN

RELATED APPLICATIONS

This application is a continuation-in-part of U.S. Application Ser. No. 07/962,097 filed Oct. 16, 1992 which is incorporated herein by reference.

BACKGROUND OF THE INVENTION

1. Field of the Invention

The present invention relates to liquid chromatography and more specifically to a method of preventing contamination of a chromatography column from particulate and dissolved contaminants.

2. Background of the Invention

Liquid chromatography is a technique which employs a stationary phase and a liquid mobile phase to separate mixtures into various components of the mixture. A separation column generally consists of small beads or particles of stationary phase that have been slurried with a solvent and then packed into column hardware to form a chromatographic bed. The separating power of a liquid chromatographic column depends upon maintaining a uniform bed of packing material free of particulate and dissolved contaminants.

The use of column protection is required, especially when analyzing dirty or contaminated samples or samples containing components which irreversibly bind to the stationary phase. Continued injections of samples containing particulate or strongly retained, non-eluting solutes will eventually degrade the stationary phase and chromatographic performance of the separating column. Degradation in column performance is evidenced by changes in peak retention times, column efficiency and column selectivity.

Conventionally, two methods have been used to protect liquid chromatographic separation columns from contamination. The first method is use of a porous frit or series of frits to capture particulate material. Frits are generally made from porous stainless steel or glass, although other materials such as porous titanium and polymers such as polyether ether ketone (PEEK) or polypropylene may be used. A frit is normally located at each end of a separation column in order to contain the particulate packing material within the column. The frit at the head of a column also serves the function of trapping particulate material. A frit normally has pores ranging in size from 0.2 to 5 μm. In addition to frits located at either end of a chromatographic column, a chromatographic system may also contain in-line frits located at various positions in the flow path. An in-line frit located between the sample injection valve and the separation column will also trap particulate material. A frit is replaced when it becomes plugged by particulate material and eluate back pressure increases to an unacceptable level.

Although useful, frits have a serious drawback. Frits have a low surface area and are inert and cannot trap or retain dissolved contaminants. Dissolved contaminants pass through the frit and are adsorbed or retained on the chromatographic stationary phase of the separation column. Continued contamination of the stationary phase degrades performance of the column.

The second method for protecting liquid separation columns is the use of guard columns or guard cartridges. A guard column or cartridge is connected in series upstream from a liquid chromatographic column to protect the separation column. The guard column is usually shorter than the separation column, but contains packing material which is similar to the stationary phase of the main separation column.

Guard columns or cartridges are inserted in the eluate fluid stream, generally between the sample injection valve and the separation column. The guard column or cartridge captures strongly retained dissolved sample components and prevents them from passing through and contaminating the separation column. The guard column or cartridge also captures particulate material. Guard columns and cartridges are extensively used and commercially available.

Despite widespread use, guard columns and cartridges have several drawbacks. Guard columns may degrade the separation efficiency and performance of chromatography columns. Column efficiency or band broadening can be affected by the flow path taken when a guard column or cartridge is used. Typically, the fluid stream travels from a sample injection valve through a tube having a small inside diameter to the guard column or cartridge, which has a relatively large inside diameter, and then back to a connecting tube having a small inside diameter and finally to the separation column which again has a relatively large inside diameter. This change in diameter of the flow path produces a broadening effect which is especially harmful in preparative columns having very large diameters.

Guard columns and cartridges contain chromatographic packing material and sample peaks can be retained slightly by this guard column material. This causes the sample peaks to broaden slightly reducing the efficiency of the separation. More importantly, guard columns and cartridges change the retention time of sample components. The change in retention times is a serious problem, especially for chromatography systems employing computer data acquisition systems. These systems rely on a peak time window to locate particular peaks.

Chromatographic separations reported in chemical literature and references typically publish retention times for peaks of interest. Use of guard columns which affect retention times increases the difficulty of matching separations to published retention times in order to verify and confirm experimental results.

Finally, the effectiveness of a guard column or cartridge is generally determined by observing the chromatographic separation. The stationary phase packing material in a guard column or cartridge is shielded from view by the column hardware. Colored contaminants can only be observed if the column end is opened, a process not recommended by most manufacturers. Opening the column disturbs the packing bed and further degrades chromatographic performance of the column. Although separation parameters such as plate number, pressure and resolution can be measured to determine the performance of a guard column or cartridge, these parameters do not always indicate whether a guard column or cartridge is adequately protecting an analytical column. Fouling of an analytical or preparative column can still take place well before there are noticeable changes in plate number, pressure and resolution.

In addition to conventional bulk powdered stationary phase packing materials traditionally used in liquid chromatography, synthetic membrane chromatography materials are also known. These membranes are generally made from synthetic or natural polymers in the form of web-type membranes, paper sheets, etc. For example, ion exchange resin beads or reversed-phase silica particles can be embedded or enmeshed in a membrane or network of polytetrafluoroethylene. These membranes are suitable for use as chromatographic stationary phase materials or as sorptive materials in filtration equipment. See for example D.F. Hagen et al, Anal. Chim. Acta, 1990, 236:157–164 and T.B. Tennikova et al, Journ. Chrom., 1991, 555:97–107.

Membrane and fabric chromatographic materials are also known in which the surface of the fabric or membrane is chemically modified to provide functional groups suitable for chromatographic separation. Examples include modified cellulose paper having weak ion-exchange groups, cross-linked vinyl polymer sheets containing ion-exchange groups, cellulose membranes having attached ligands for affinity chromatography. Membranes have also been prepared by polymerization of glycidyl methacrylate and ethylene-dimethacrylate to produce membranes having surface epoxide groups. The epoxide groups are then modified to provide a solid phase material suitable for protein separation. See T.B. Tennikova et al, Journ. Liq. Chrom., 1990, 13:63–70.

A need continues to exist for improved methods of protecting liquid chromatography columns. There is a particular need! for methods of protecting liquid chromatography columns which do not substantially alter the retention time of sample peaks, do not contribute to substantial peak broadening and yet provide adequate protection for analytical and preparative columns.

SUMMARY OF THE INVENTION

Accordingly, one object of the present invention is to provide a method of protecting a liquid chromatography column from contamination by particulate and dissolved contaminants.

A further object is to protect the liquid chromatography column using a method which does not substantially change peak retention times or contribute to significant peak broadening.

Another object is to provide a method of protecting liquid chromatography columns using a protection means which is inexpensive and allows one to observe the condition of the protecting means without disturbing chromatographicmaterial.

These and other objects which will become apparent from the following specification have been achieved by the present method of preventing contamination of a liquid chromatography separation column containing stationary phase chromatographic material from particulate or dissolved contaminants in a sample stream. In the present method, particulate or dissolved contaminants are retained using a thin protective pad or disk located upstream from the separation column, where the protective pad or disk comprises a sorptive chromatographic material in fabric or membrane form. The sorptive protective pad does not affect or harm the chromatographic separation performed on the separation column. The guard disk can be incorporated into chromatographic apparatus in a suitable holder.

DETAILED DESCRIPTION OF THE PREFERRED EMBODIMENTS

It has now been discovered that a thin protective layer of sorptive chromatographic material in the form of a fabric or membrane is effective in protecting a liquid chromatography column from particulate and dissolved contaminants without substantially affecting the retention time or peak width of sample peaks. The protective layer of the present invention is positioned upstream from the separation column which is to be protected. That is, a fluid stream containing sample will pass first through the protective layer before passing through the chromatography separation column.

There is no particular limitation on the shape of the protective layer which may be square, rectangular, circular, etc. Further, the protective layer of the present invention may have a single layer or may have a plurality of layers depending upon the desired thickness of the pad or disk. A particularly preferred form of the protective layer is a guard pad or guard disk capable of complementary positioning in a liquid chromatography system, preferably a medium or high pressure system. For simplicity, the protective layer of the present invention will be referred to below as simply a "guard disk", a particularly preferred embodiment of the present invention.

Figure 1:
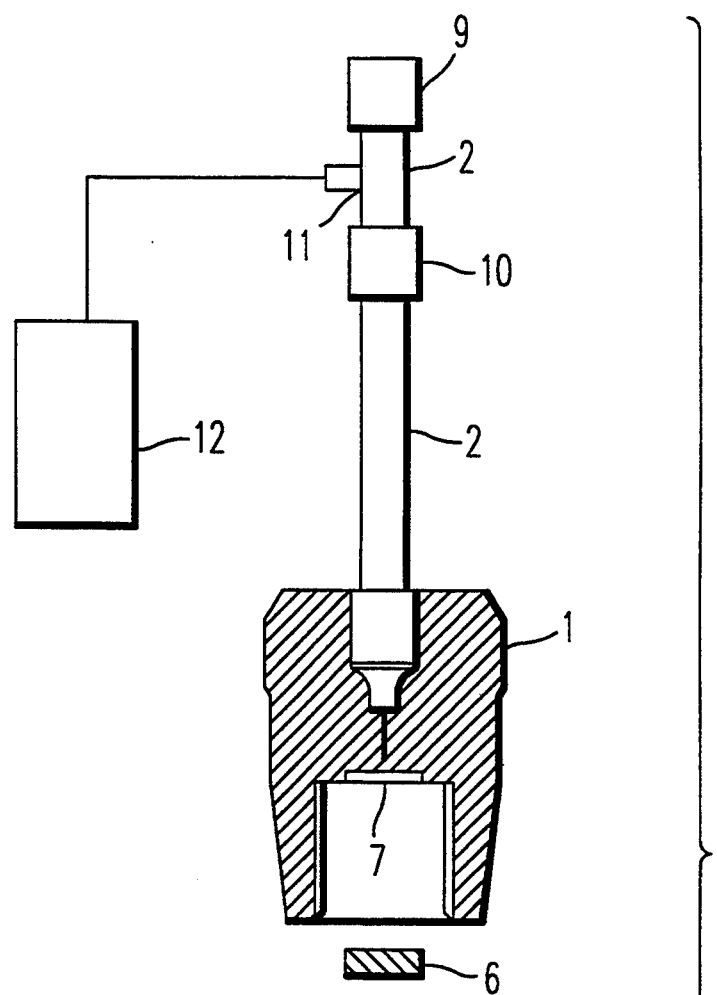
FIG. 1 shows the position of a guard disk located between a chromatographic column and a column top.
Figure 1:
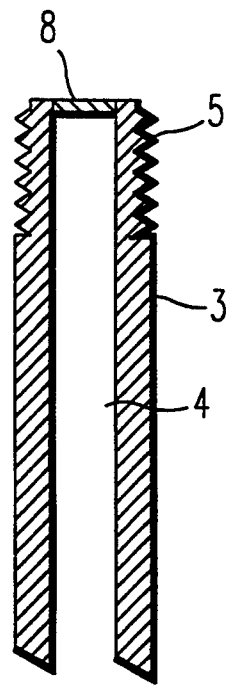

FIG. 1 shows an embodiment in which the guard disk is in direct contact with the top portion of a chromatographic separation column. Column top 1 has conventional fittings for receiving eluate solvent and sample through inlet tubing 2. The column top or cap 1 is fitted and sealably attached to column body 3 containing chromatographicbed 4 using a conventional fitting 5 (e.g. threaded) or any equivalent fitting capable of tightly sealing the column top to the column body. The column top 1 is adapted to receive guard disk 6 in a sealing cavity 7. Preferably, the column body has a column frit 8 at the upstream end of chromatographic bed 4 to prevent disturbance of the chromatographic bed when the column top is removed to observe the guard disk. In this embodiment, the guard disk will contact the frit.

In operation, solvent pump 9 pumps elution solvent to sample injector 10 and into column top 1 through tubing 2. The elution solvent passes through guard disk 6 and then through frit 8 before entering chromatographic bed 4. Eluate pressure upstream from the guard disk is measured by pressure transducer 11 which is electrically connected to a display device 12.

Figure 2:
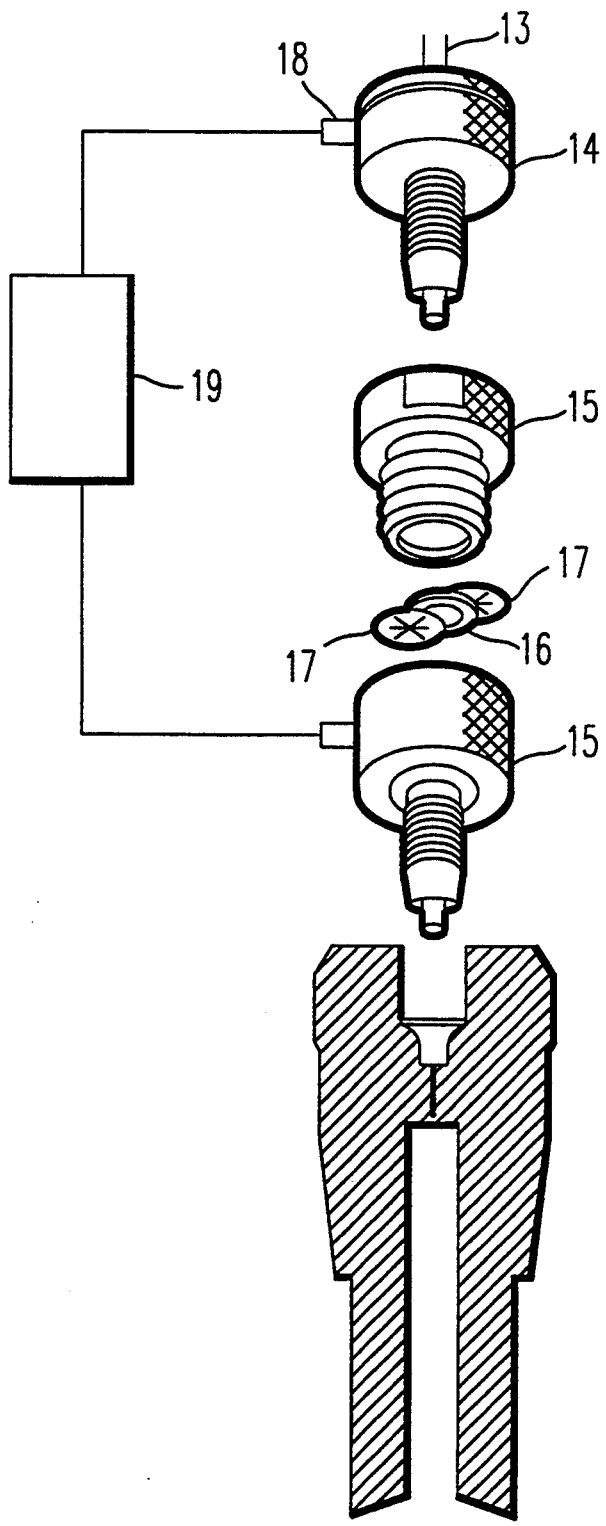
FIG. 2 shows an exploded view of a liquid chromatography column incorporating the guard disk of the present invention.

FIG. 2 shows the positioning of the guard disk of the present invention for inline protection of a separation column. FIG. 2 also shows a preferred embodiment of the chromatographic hardware suitable for use in holding the guard disk of the present invention for inline application. However, the present invention is not limited to the specific hardware shown in FIG. 2. Any suitable means for holding and positioning the guard disk for inline protection in conventional liquid chromatography equipment may be used in the present invention, i.e., conventional frit holding hardware.

In FIG. 2, high pressure liquid chromatography (HPLC) tubing or conduit 13 is connected to a conventional HPLC fitting 14 having a threaded male end. Fitting 14 is connected to a guard disk holder 15 adapted to hold the guard disk 16 inline substantially perpendicular to the eluate solvent flow through the guard disk holder. If desired, distribution disks 17 may be used above or below the guard disk to more effectively distribute the eluate solvent and sample passing through the guard disk. Disk holder 15 can then be directly connected to the column top which is mounted onto the column body. Preferably, the disk holder is threaded into the column top. The column top is also preferably threadably mounted onto the column body. Pressure transducer 18, for measuring the eluate pressure drop, is mounted through, preferably threadably mounted through, fitting 14 and provides input to display, analyzer or microcomputer 19.

In its preferred form, the guard disk is circular having a rigid annular outer ring or collar for easy handling. The annular ring may be constructed of any suitable material which is inert to the chromatographic separation. Any inert conventional engineering plastic may be used. The invention is not limited by the specific type of polymer used in the annular ring so long as the material is inert to the eluate solvent and sample and has sufficient dimensional stability. Preferably, the inside diameter of the annular ring corresponds to the inside diameter of the column body and therefore the column separation bed.

The rigid annular outer ring of the guard disk may comprise a single rigid annular outer ring encircling a disk-shaped pad of guard disk material. In this embodiment of the invention shown in FIG. 3A, one or more pads of guard disk material 20 are placed in the rigid annular ring 21. For example, the fabric may be cut to a circular diameter which securely contacts the inner diameter surface of the annular ring. As the disk holder is tightened against the disk, the top and bottom surfaces of the holder seal against the collar of the guard disk. Sealing pressure from the guard disk holder is, therefore, applied against the collar of the disk which prevents the material of the guard disk pad from being crushed.

Figure 3B:
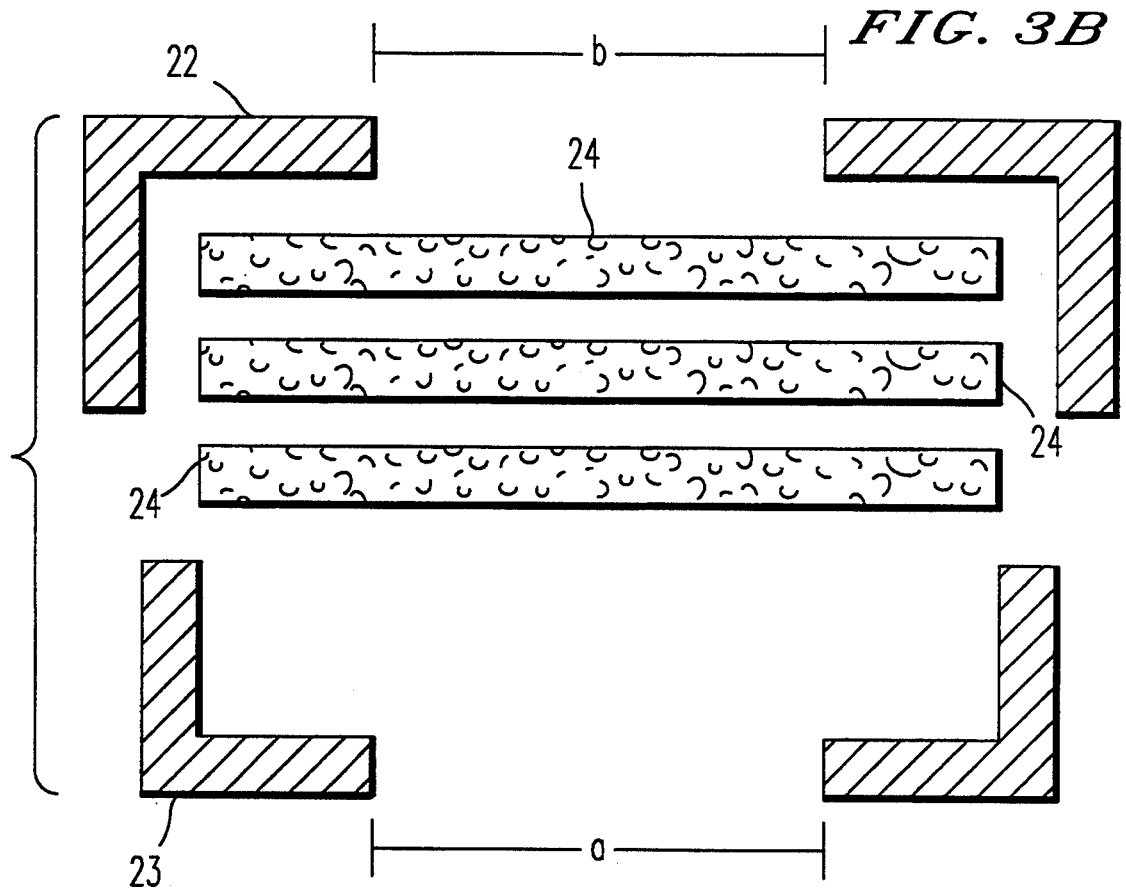
FIG. 3B is an exploded view of a guard disk having a two-piece annular ring and containing three pads of guard disk material.
Figure 3C:
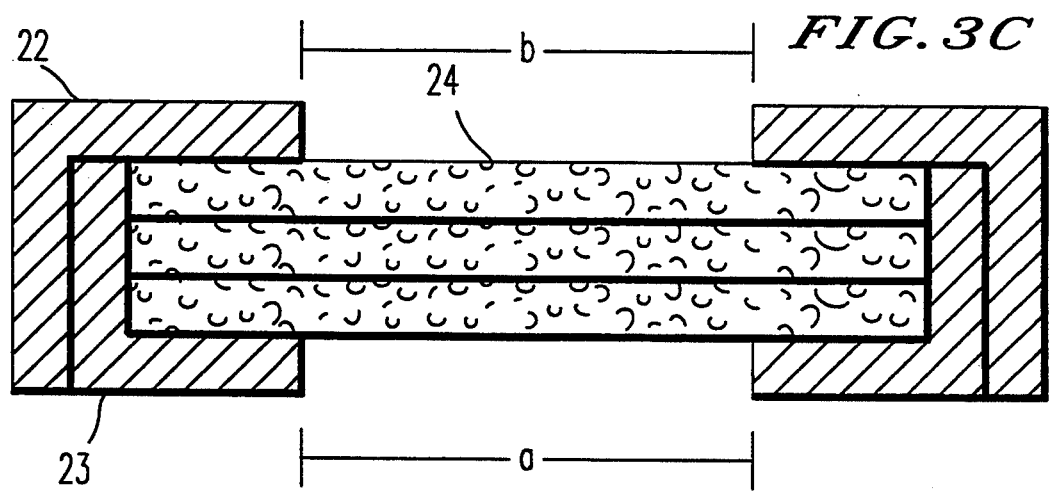
FIG. 3C shows an assembled view of the guard disk of FIG. 3B.
Figure 3A:
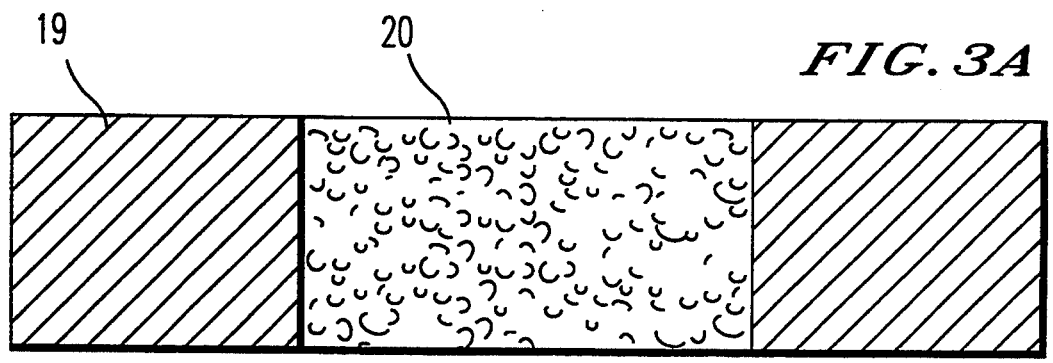
FIG. 3A shows a guard disk having a one-piece annular ring.

Alternatively, the rigid annular outer ring may comprise two flanged rings as shown in FIGS. 3B and 3C, an outer flanged ring 22 and an inner flanged ring 23, where the innerflanged ring is insertable within the flange of the outer ring forming a press-fit two piece collar around one or more pads of guard disk material 24. In a preferred embodiment, the inner diameter (a) of the inner flanged ring will have the same diameter as the separation column bed as indicated above.

In the two-piece annular ring embodiment shown in FIG. 3C, one or more pads of guard disk material 24 having a diameter greater than the inner diameter (b) of the outer flanged ring 22 are positioned within the flanges of the outer ring. The inner flanged ring 23 is then inserted into the outer ring to form a press-fit two-piece annular ring in which the guard disk pad(s) is (are) frictionally held within the press-fit ring or collar. In a more preferred embodiment, the inner diameter (b) of the outer flanged ring and the inner diameter (a) of the inner flanged ring are substantially the same.

In still another embodiment, the rigid annular outer ring may be incorporated into the guard disk holder or chromatographic column cap. The annular ring is a flange that is part of one or both sides of the disk holder or the column cap. In this embodiment, the guard disk does not have an outer ring. A circle of the guard disk sheet material is placed into the holder or column cap. The flange in the holder column cap is annular so that when the holder or column cap is tightened, the flange pinches or seals the outer annular portion of the guard disk. The center portion of the guard disk not pinched is in a chamber or depression in the holder or cap. Fluid flows through the center portion allowing the guard disk to retain particulate or strongly adsorbed material, but fluid cannot flow around the disk or past the edges.

The function of the guard disk is exactly the same as when the collar is part of the guard disk itself. However in this case the collar is part of the holder or column cap.

The guard disk of the present invention comprises a layer or pad of sorptive chromatographic material which has been incorporated into a fabric or membrane. The term "incorporated into a fabric or membrane" means that the sorptive chromatographic material is encapsulated by or trapped within a fabric or membrane, is stabilized within a fabric or membrane or is covalently attached to a fabric or membrane such that the sorptive chromatographic material does not exist as free flowable particulate bulk material and is not separable from the guard disk under liquid chromatography conditions. The term "sorptive" means that the material is capable of absorbing, adsorbing or otherwise entrapping or retaining dissolved contaminants from the sample stream.

When the sorptive material is incorporated into a fabric, the fabric may be woven or nonwoven. The spaces between fibers of the fabric should be small enough to prevent sorptive particulate material from passing through the fabric. The density of non-woven fibers and the density of warp and weft fibers of woven fabric can be routinely adjusted to provide the desired density and porosity.

Membrane materials for use as the sorptive chromatographic material are known in the art and can be prepared by polymerizing suitable ethylenically unsaturated monomers using known methods, i.e. radical polymerization. Suitable monomers include $C_{2-5}$ olefins, halogenated olefins, in particular chlorine and fluorine substituted $C_{2-4}$ olefins (meth)acrylic acid, $C_{1-4}$ alkyl(meth)acrylates, glycidyl (meth)acrylates, etc. Membranes prepared by condensation reactions of monomers containing amino, hydroxyl, carboxylic acid, acid chloride and anhydride groups, for example, to prepare polyamide membranes, polyester membranes, etc may also be used in the present invention. Further, naturally occurring polymers such as cellulose may be used.

The fabric or membrane may be made of any suitable material so long as the material is porous and inert under liquid chromatography conditions. Generally, the fabric or membrane will be made of a porous synthetic or natural polymeric material. Suitable fabric or membrane materials include polytetrafluoroethylene (PTFE), cellulose, polyvinyl chloride (PVC), nylon, etc. Fabric and membranes prepared from these materials are well known in the art. See, for example, Anal. Chim. Acta, 1990, 236:157–164; Journ. Chrom., 1991, 555:97–107 and Anal. Chem., 1992, 64:820–822. Any of the fabric and membrane materials known in the art may be used in the present invention.

Typical stationary phase chromatographic materials that may be used as sorbents include reverse phase, ion exchange, ion exclusion, chelation and affinity materials. For example, octyl and octadecyl bonded silica materials are sold by numerous chemical and chromatography supply companies. Chelating and ion exchange materials are also well known and commercially available. For example, a typical chelating material is CHELEX 100 (available from BioRad), and typical ion exchange materials are anion exchangers in the DOWEX-1 series and cation exchangers in the DOWEX-50 series (available from Dow Chemical Co.).

Additionally, specific fabric and membrane stationary phase materials include BIO-REX ion-exchange membranes (available from BioRad) containing standard chromatographic material in bead form embedded in a web of polytetrafluoroethylene and EMPORE membranes containing octyl and octadecyl-bonded silica particles enmeshed within polytetrafluoroethylene fibers (available from 3M Company).

Alternatively, the guard disk may be a fabric or membrane matrix having stationary phase functional groups covalently bonded to the fabric or membrane structure itself. Ion exchange anionic functional groups such as carboxyl, carboxymethyl, sulfate, sulfonate and phosphonate groups; and cationic exchange functional groups such as dialkylaminoalkyl groups, e.g., diethylaminoethyl (DEAE) and quaternary alkyl ammonium groups such as methyltrimethyl and methyldimethyl aminoethanol groups, may be covalently bonded to the fabric or membrane.

Specific fabrics or membranes having surface functional groups include cellulose paper modified to contain ion-exchange groups such as the materials described in U.S. Pat. No. 4,663,163 and U.S. Pat. No. 4,639,513, cellulose membranes with attached affinity ligands including MEMSEP membranes (Milipore Co.) and MEMTEC and ABSORBENT G membranes (Genex Co.). It is also possible to use the synthetic membranes having surface epoxide groups described by Tennikova et al where the surface epoxide groups are modified to form affinity ligands for affinity chromatography.

The amount of sorptive chromatographic material present in the guard disk is substantially less than the amount of stationary phase material in the separation column. Preferably, the amount of sorptive material is such that the guard disk does not increase the retention time of a sample more than 5% relative to the retention time of the sample on an identical column without the guard disk.

Generally, the amount of sorptive material in the guard disk relative to the amount of stationary phase material in the separation column will be in the range of about 0.05-2 wt. %, preferably about 0.1-1 wt. %. The guard disk will generally have a thickness ranging from about 0.5 to 20 mm, preferably about 0.5-10 mm. However, very long (about 0.5-5 meters) preparative or industrial separation columns may require thicker (1-5 cm) sorptive guard disks. Guard disks having these dimensions do not contribute significantly to chromatographic separation and will not increase the retention time of sample peaks more than about 5%.

In order to retain particulate contaminants, the fabric or membrane must be porous, where the pore size of the fabric or membrane is smaller than the particulate to be retained. In general, membrane or fabric pore sizes in the range of 0.1-5 $\mu$m, preferably 0.5-2 $\mu$m are suitable for liquid chromatography systems. Specific useful pore sizes include 0.2, 0.5, 2 and 5 $\mu$m pores.

In order to retain dissolved, strongly retained contaminants, the guard disk must contain sorptive material. In many cases, the guard disk sorptive material will be similar or the same in selectivity to the stationary phase of the separation column. For example, a particular octadecyl-bonded silica incorporated into a guard disk may be used with several different types of commercial ocladecyl-bonded silica reverse phase columns without affecting the chromatographic separations. The sorptive material in the guard disk may be identical to the stationary phase in the separation column. Thus, dissolved contaminants which would irreversibly adsorb to the separation column are first retained by the guard disk.

A guard disk may contain sorptive material different from the separation column, but designed to remove specific contaminants. For example, a guard disk containing chelating ion exchange groups may remove metals that may contaminate silica sites on a normal phase separation column. Even if the guard disk material is different from the separation column, the effect on the separation is small. This is due to the small relative thickness of the guard disk to the column.

It is critical that the sorptive material in the guard disk be compatible with the stationary phase of the separation or analytical column. The term "compatible" as used herein means that the selectivity of the sample compounds for the sorptive material in the guard disk is similar to or lower than the selectivity of the sample compounds for the separation column. For example, when ion chromatography separations are performed with a low capacity ion exchange separation column, the capacity of the ion exchange resin in the guard disk should be equal to or lower than the ion capacity of the separation column. Use of a high capacity resin in the guard disk may result in the undesirable retention of sample peaks. The use of a compatible sorptive material in the guard disk ensures that any component which is injected into the chromatographic stream which would adsorb and contaminate the separation column will also be retained by the guard disk.

Additionally, the guard disk must be compatible with the eluate solvent used in the chromatography. Use of specific solvents with given chromatographic materials is well known in the art and can be easily determined. For example, it is well known that TEFLON fabrics and membranes will not swell or shrink when exposed to organic solvents which are traditionally used in reversed-phase liquid chromatography.

The guard disk of the present invention is substantially different than conventional guard columns or guard cartridges and has several advantages over these conventional systems.

1. The guard disk of the present invention contains substantially less chromatographic material than conventional guard columns or cartridges and therefore has little or no effect on chromatographic separation and sample peak retention.

2. The guard disk of the present invention is superior to conventional frits which do not contain sorptive chromatographic material. Conventional frits can remove only particulate material but cannot adsorb dissolved contaminants.

3. The guard disk of the invention does not require tubing and fittings having a smaller inside diameter than the separation column. Peak broadening, associated with sample fluid flowing between narrow fittings and wider columns is therefore reduced. The guard disk can be exactly the same diameter as the separation column bed. This makes the flow path from the guard disk to the separation column direct and smooth without disruption and with minimal peak broadening. Since the guard disk is thin, the guard disk has substantially less void volume than a guard column or cartridge and therefore contributes less to peak broadening.

Thin guard disks having the same diameter as the separation column bed are particularly useful for preparative columns, especially columns having very large diameter chromatographic beds (e.g. 25 cm). However, the guard disk diameter does not need to be exactly the same diameter as the separation column. Use of a smaller diameter guard disk is useful in avoiding peak broadening. However, a larger diameter guard disk may be useful in particular applications since a larger diameter disk will have a larger capacity in retaining particulate and dissolved contaminants.

4. The guard disk of the present invention does not contain free bulk particulate stationary phase material. The use of sorptive material in the form of a fabric or membrane enables the guard disk to be much thinner than conventional guard columns or cartridges.

There are substantial difficulties in packing bulk particulate stationary phase materials into a short column having a length of 5 mm or less. Conventional packing of particulate stationary phase materials requires formation of a slurry of the stationary phase followed by loading of the slurry into the guard column or cartridge under pressure. After the column has been loaded, the upper surface of the stationary phase is scraped flat to enable fitting of the column top or cartridge cap. The margin of error in flattening the surface of the column is generally in the range of about 0.5-1 mm. In fact, a common procedure for packing a column is to remove the packed column from the packer and then leave a mound of several millimeters before placing the endcap on the top of the column. This large margin of error prevents the use of smaller guard columns and cartridges.

5. Unlike a conventional guard column or guard cartridge, the guard disk of the present invention can be examined directly and easily to determine if colored, strongly retained material is being removed from the samples injected. Frequently, contaminants have a different color than the disk and it is easy to determine if these contaminants are being trapped by the guard disk.

As discussed below in more detail, the guard disk of the present invention is easily removed from the chromatographic apparatus, can be examined visually and replaced with a new disk, if necessary, without disturbing the separation column bed itself. The bottom of the guard disk can be examined to see if contaminants are breaking through the disk into the separation column. In this manner, it is easy to determine the lifetime of the guard disk.

In contrast, conventional guard columns and cartridges use opaque or translucent casing material to enclose particulate stationary phase. It is difficult or impossible to visually determine the lifetime of these columns and cartridges. With conventional guard columns and cartridges, column lifetime is established by injecting samples until the separation changes or becomes distorted. The separation and guard columns must then be regenerated or replaced.

Another preferred method for determining the useful lifetime or the extent of fouling of the guard disk is to place a pressure transducer on the inlet side (upstream) and optionally the outlet side (downstream) of the guard disk.

Many high pressure liquid chromatography (HPLC) systems measure eluate back pressure using a pressure transducer. The transducer is generally a flush mount transducer mounted through a bore in a chromatographic fitting or housing such that a diaphragm is in contact with the eluate. Typically, the diaphragm is made of stainless steel to prevent corrosion and reaction with the eluate. The diaphragm is electrically connected to an analyzer, e.g., a microcomputer or microprocessor, or simply electrically connected to a display device which is capable of displaying the pressure (psi) sensed by the transducer. Such transducers are available commercially, for example, from Omega Engineering, Inc., Stamford, CT.

In the present invention, a single pressure transducer may be placed in line on the upstream or inlet side of the guard disk to measure eluate pressure upstream from the guard disk. Preferably, the transducer is positioned upstream from the sample injector and downstream from the solvent pump. Locating the pressure transducer before the sample injector produces the least broadening effect on chromatographic peaks. In this embodiment, total eluate back pressure is measured. This back pressure includes the guard disk back pressure and the separation column back pressure. When the combined back pressure exceeds a predetermined value, the guard disk is replaced. The specific back pressure threshold value will obviously depend upon the specific chromatographic system, diameter of chromatography fittings and tubing and the frequency with which one wishes to replace the guard disk. For example, if the guard disk back pressure is about 50 psi and the separation column back pressure is about 500 psi, the total back pressure resulting from the separation column and a new guard disk will be about 550 psi. When the back pressure increases to about 600 psi, the guard disk could be replaced.

In a further embodiment, pressure transducers are located on both the upstream and downstream sides of the guard disk. Again, the pressure transducers are electrically connected to a display or an analyzer. This embodiment allows one to calculate the pressure drop across the guard disk itself. The upstream pressure transducer measures the fluid pressure upstream from the guard disk while the downstream transducer measures the fluid pressure downstream from the guard disk. Mathematically subtracting the lower pressure from the higher pressure provides the pressure drop across the guard disk. The mathematical subtraction can be routinely accomplished using conventional analyzers, microprocessors or microcomputers and displayed. The pressure drop caused by a new cartridge is quite low due to the thinness of the sorptive material in the guard disk. When the pressure drop increases above a preset value the guard disk is replaced. For example, when the eluate pressure drop across the guard disk doubles, the guard disk would be replaced. This embodiment has the advantage of measuring only the pressure drop contributed by the guard disk. Back pressure contributed by the separation column or clogging of the separation column is not considered.

The position of the downstream pressure transducer can be at any location on the downstream side of the guard disk including the outlet end of the separation column. The preferred position of the downstream pressure transducer is at the interface between the guard disk and the separation column.

The guard disk of the present invention may be incorporated into a liquid chromatographic system in two forms, i.e. as an inline filter or as the top portion of a chromatographic separation column. When used as an inline filter, conventional hardware used to hold an inline frit may be used. The guard disk may be positioned in any location in which a conventional frit would be used, i.e., between a sample injection port or loop and the separation column, between a pump and the sample injector, between a solvent reservoir and a pump, etc.

Other features of the invention will become apparent in the course of the following descriptions of exemplary embodiments which are given for illustration of the invention are not intended to be limiting thereof.

EXAMPLES

Example 1

A guard disk was fabricated from underivatized, neutral 8 μm macroporous styrene/divinyl benzene beads (415 m$^2$/g surface area) obtained from Sarasep, Inc.) and a TEFLON polymeric fabric (3M Company). An 8 mm diameter, 0.6 mm thick guard disk of this material in an inline holder was used to guard an AN1 ion chromatography column (Sarasep, Inc.). The eluate was 1.7/1.8 mM sodium bicarbonate/carbonate with a flow rate of 1 mL/min. The AN1 separation column used the same macroporous beads as the guard disk. Injections of 20 μl Trypan Blue dye into the guard disk showed that the dye was retained in an effective 4 mm diameter with no breakthrough into the column.

Example 2

Figure 4A:
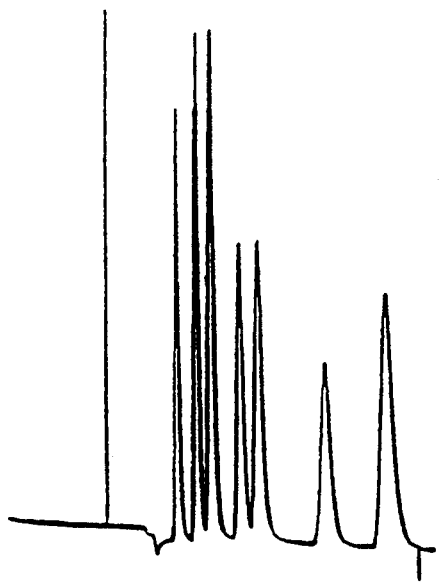
FIGS. 4A, 4B and 4C compare ion chromatography separation of anions using a control column with no guard disk or guard column, the same column with a guard disk and the same column with a guard column.

An AN300 anion exchange separation column (Sarasep, Inc.) having 0.05 mequiv./g capacity was used to determine the ability of the guard disk of the present invention to protect a separation column and to compare the performance of the guard disk with a conventional guard column and a control non-guarded column. The eluate was 1.7/1.8 mM sodium bicarbonate/carbonate used at a flow rate of 2.0 mL/min. A sample containing 5 ppm fluoride ions, 10 ppm chloride ions, 20 ppm nitrite ions, 20 ppm bromide ions, 20 ppm nitrate ions, 30 ppm phosphate ions and 20 ppm sulfate ions was injected with a 20 microliter injection loop. The ions were separated and eluted from the column in the order stated as shown in FIG. 4A.

Figure 4B:
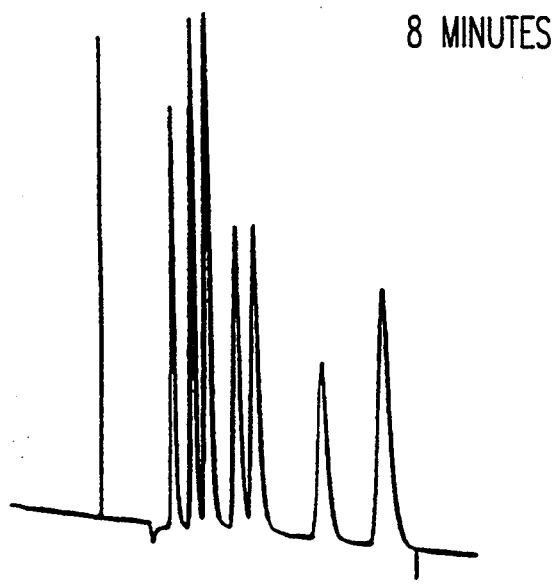

A guard disk pad of 4.6 mm outside diameter (o.d.) and containing the neutral, high surface area guard disk material of Example 1 at a thickness of 1.8 mm was placed in a plastic collar (PEEK) having dimensions 6.0 mm o.d.×1.8 mm thick with a 4.6 mm inside diameter (i.d.) center. The guard disk was placed inline with the AN300 column using the holder shown in FIG. 2. The results of a separation using this system are shown in FIG. 4B. FIG. 4B shows that there was no change in resolving power or retention time using the guard disk of the present invention.

Figure 4C:
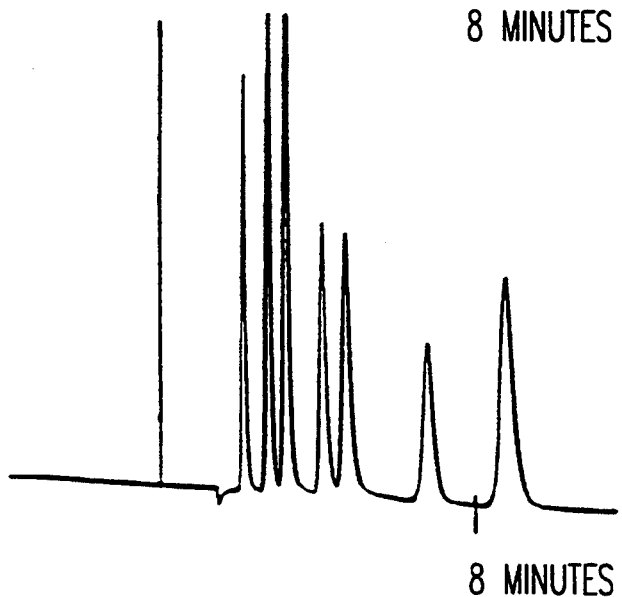

For comparison, a 4.6×50 mm AN guard column (Sarasep, Inc.) containing the same packing as the AN300 separation column was substituted for the guard disk described above. The results of ion chromatography using this system are shown in FIG. 4C. FIG. 4C shows that the retention times of sample peaks, in particular sample peaks having longer retention times is increased substantially.

Example 3

Figure 5A:
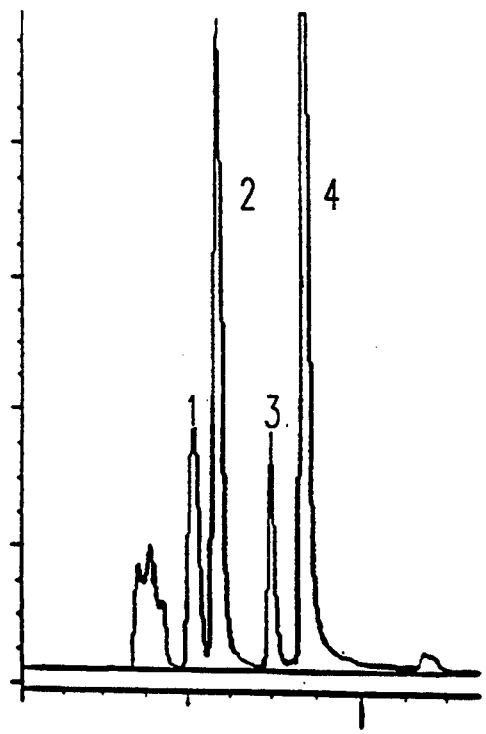
FIGS. 5A and 5B compare the separation of organic compounds on a reverse phase chromatography column with and without the guard disk of the present invention.
Figure 5B:
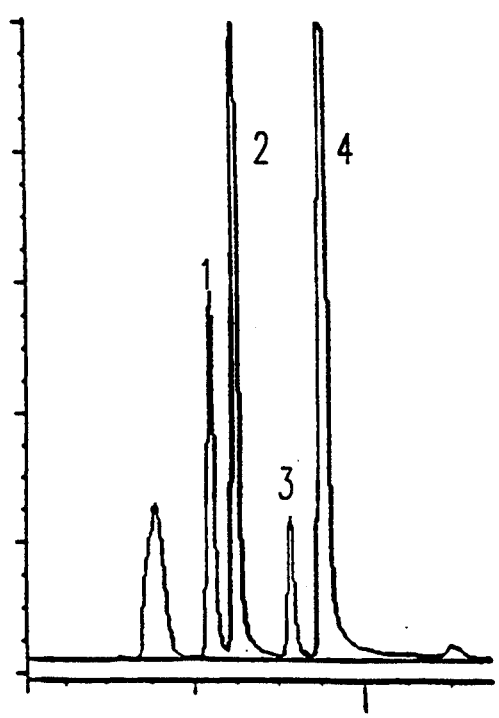

A guard disk having the dimensions of the guard disk described in Example 2 was prepared for use in a reversed-phase chromatographic system. The guard disk contained octadecyl (C18) silica-based reversed-phase stationary phase material woven into a TEFLON polymer fabric (3M Company). A column (4.6 mm×150 mm) containing C18 reversed-phase stationary packing material (SPHERISORB ODS-2, 5 micron packing, MetaChem Technologies, Inc.) and the guard disk were used with a 80/20 percent (v/v) acetonitrile/water eluate at 1 ml/min. A mixture of uracil, acetophenone, methyl benzoate and toluene were separated using this system. The reverse-phase chromatographic system resolved four individual peaks as shown in FIGS. 5A and 5B. No degeneration was seen in sample peak separation or resolving power. No change was seen in sample peak retention times. Additionally, separation of the mixture was not affected when the guard disk was placed at the head of the column bed as shown in FIG. 1.

Example 4

A guard disk material containing macroporous poly (styrene/divinylbenzene) was placed into a two piece annular collar. The outer diameter of the collar was 6.35 mm. After assembly of the two piece collar the guard disk had a thickness of 1.7 mm. Allowing for the sealing portion of the collar where the guard disk material is pinched, the effective center diameter of the guard disk material was 3.63 mm. In this example, both sections of the collar were tan colored PEEK (polyetheretherketone). In other examples, the collar may be assembled with two different colored annular rings. In this way, the direction of flow through the guard disk may be established and maintained, even if the guard disk is removed from the holder, by repositioning the disk in the same orientation.

The guard disk was placed in a holder and a solution of 0.1 mg/mL methylene blue indicator was pumped through the disk at a flow rate of 1 mL/min. Methylene blue was completely retained by the guard disk. After about 10 mL was pumped through the disk, the disk was removed and then sliced in half so that the cross section of the disk was exposed. The adsorption of the dye indicated that the flow through the disk was through the center with approximately a 2 mm diameter. All of the flow was through the center. Because the outer edge of the guard disk material was pinched by the collar, no dye was able to bypass the guard disk material.

Obviously, numerous modifications and variations of the present invention are possible in light of the above teachings. It is therefore to be understood that within the scope of the appended claims, the invention may be practiced otherwise than as specifically described herein.

WHAT IS CLAIMED AS NEW AND DESIRED TO BE SECURED BY LETTERS PATENT OF THE UNITED STATES IS:

1. A method of preventing contamination of a chromatography separation column containing stationary phase chromatographic material, by particulate or dissolved contaminants in a sample stream, comprising:

retaining particulate and dissolved contaminants in a protective pad by passing the sample stream through the protective pad before the sample stream contacts the separation column, wherein said protective pad comprises a fabric or membrane sorptive chromatographic material.

2. The method of claim 1, wherein said protective pad comprises a plurality of fabric or membrane layers.

3. The method of claim 1, wherein said protective pad comprises particulate sorptive chromatographic material encapsulated within a fabric or membrane.

4. The method of claim 3, wherein the amount of sorptive material in the protective pad relative to the amount of stationary phase material in the separation column is in the range of about 0.05-2 wt. %.

5. The method of claim 4, wherein the relative amount of sorptive material in the protective pad is about 0.1-1 wt. %.

6. The method of claim 1, wherein said protective pad comprises a fabric or membrane having chromatographically or sorptively effective functional groups covalently bonded thereto.

7. The method of claim 1, wherein said retaining step does not increase the retention time of a sample passing through the protective pad and separation column by more than 5% relative to the retention time of said sample passing through the separation column alone.

8. The method of claim 1, wherein said protective pad has a thickness ranging from about 0.5-20 mm.

9. The method of claim 8, wherein said protective pad has a thickness ranging from about 0.5-10 mm.

10. The method of claim 1, wherein the protective pad and separation column contain the same chromatographic material.

11. The method of claim 1, wherein the protective pad and separation column contain different chromatographic materials.

12. The method of claim 1, wherein said protective pad comprises a membrane having covalently bonded chromatographic or sorptive functional groups.

13. The method of claim 1, wherein the separation column is in a chromatography system having a sample stream conduit between a sample injection means and the separation column, further comprising positioning said protective pad in said sample stream conduit.

14. The method of claim 13, wherein the chromatography system comprises a holder for positioning said protective pad in said sample stream, the holder having an annular flange for sealably contacting said protective pad.

15. The method of claim 1, wherein the separation column is in a chromatography system having a pump in fluid connection with a sample injection means and the separation column, further comprising positioning said protective pad between the pump and injection means.

16. The method of claim 1, wherein the separation column is in a chromatography system having a solvent reservoir in fluid connection with a pump and the separation column, further comprising positioning said protective pad between the solvent reservoir and the pump.

17. The method of claim 1, wherein the separation column has a column body and a column cap, wherein the column cap has an annular flange for sealably contacting said protective pad.

18. The method of claim 1, wherein said protective pad is a disk having a thickness of about 0.5-20 mm.

19. The method of claim 1, wherein said protective pad is a disk having a thickness of about 0.5 to about 5 mm.

20. The method of claim 1, wherein the top of the separation column has a frit and said protective pad is positioned in contact with said frit.

21. The method of claim 1, wherein the separation column is in a chromatography system having a fluid pressure transducer, further comprising positioning said protective pad downstream from said transducer.

22. The method of claim 21, wherein the chromatography system has two fluid pressure transducers, further comprising positioning said protective pad between said transducers.

* * * * *